United States Patent [19]

Muccio et al.

[11] Patent Number: 5,094,783
[45] Date of Patent: Mar. 10, 1992

[54] RETINOID COMPOUNDS

[75] Inventors: Donald D. Muccio, Hoover; Wayne J. Brouillette, Birmingham, both of Ala.

[73] Assignee: UAB Research Foundation, Birmingham, Ala.

[21] Appl. No.: 546,189

[22] Filed: Jun. 29, 1990

[51] Int. Cl.$^5$ ............................................. C11C 1/00
[52] U.S. Cl. .................................. 260/413; 562/510; 568/827
[58] Field of Search ........................... 260/410.6, 413; 562/510; 568/827; 514/725, 731

[56] References Cited

PUBLICATIONS

Robinson et al., "Reactions of Vinylogous Phosphonate Carbanions and Reformatsky Reagents with a Sterically Hindered Ketone and Enone", *Journal of Organic Chemistry*, vol. 54, May, 1989, 1992-1997.

Primary Examiner—José G. Dees
Assistant Examiner—Deborah D. Carr
Attorney, Agent, or Firm—Wegner, Cantor, Mueller & Player

[57] ABSTRACT

Retinoid compounds with bioactive properties and their synthesis are described. The compounds are useful as chemopreventive or cancer-treating agents and dermatological agents. The novel retinoids are members of either of the two general structures:

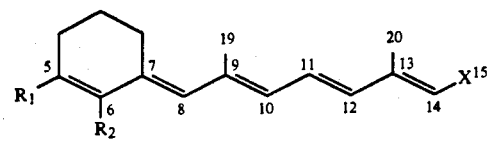

(I)

or

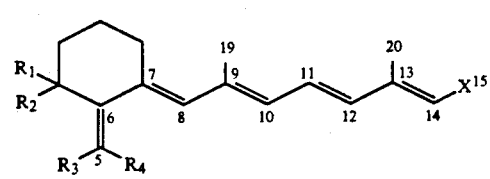

(II)

wherein X is $CO_2H$ or $CH_2OH$; and in formula (I), $R_1$ and $R_2$ are each hydrogen, a $C_{1-4}$ alkyl, a $C_{1-4}$ alkoxy, or $R_1$ and $R_2$ taken together form a 5- to 7-membered cycloalkyl or cycloalkenyl ring; and in formula (II), $R_1$ and $R_2$ are each hydrogen, a $C_{1-4}$ alkyl, a $C_{1-4}$ alkenyl or a $C_{1-4}$ alkoxy, or $R_2$ and $R_3$ taken together form a 5- to 7-membered cycloalkyl or cycloalkenyl with $R_1$ and $R_4$ being a hydrogen atom, a $C_{1-4}$ alkyl, a $C_{1-4}$ alkenyl or a $C_{1-4}$ alkoxy.

17 Claims, 1 Drawing Sheet

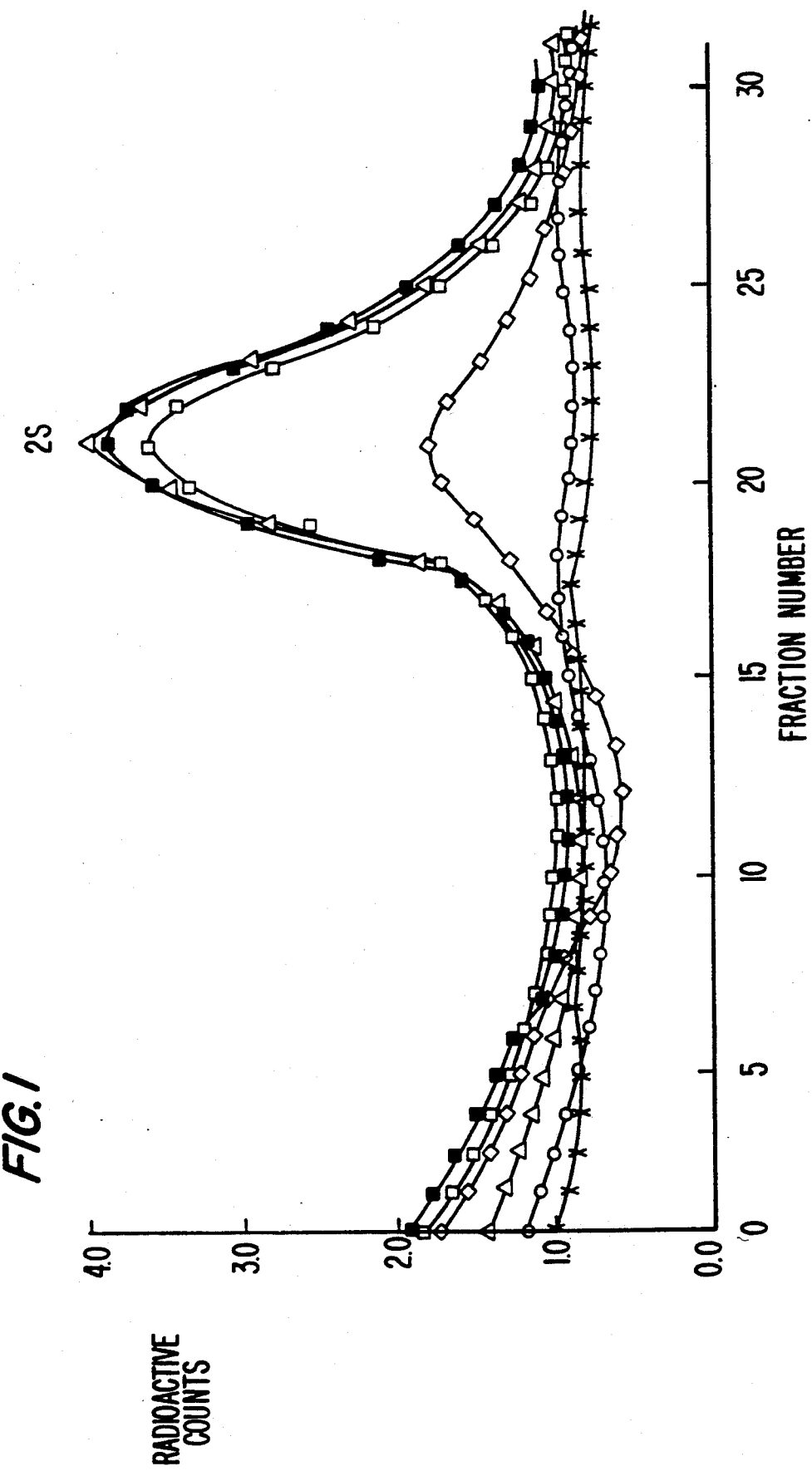

RETINOID COMPOUNDS

BACKGROUND OF THE INVENTION

The present invention relates to novel pharmaceutical compounds and their synthesis, the compounds being retinoids having utilities analogous to those for naturally-occurring vitamin A.

Vitamin A naturally occurs in three common forms, vitamin A alcohol (retinol), vitamin A aldehyde (retinal) and vitamin A acid (retinoic acid). All forms are isoprenoid compounds containing a six-membered carbocyclic ring and an eleven-carbon side chain.

Vitamin A occurs in solution as a mixture of nearly planar 6-s-trans and distorted 6-s-cis conformations, with the latter conformation predominating (shown below for retinal):

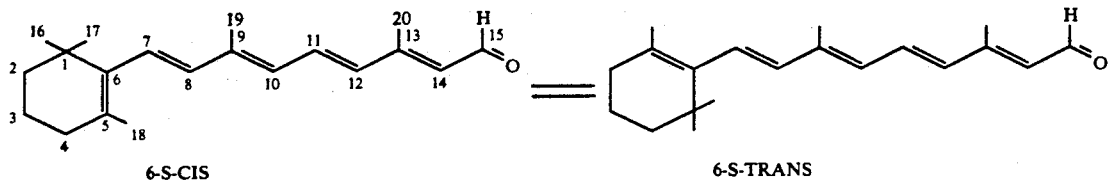

6-S-CIS       6-S-TRANS

An analog of retinal has been proposed which has a conformationally-defined, distorted 6-s-cis geometry (see Robinson et al., "Reactions of Vinylogous Phosphonate Carbanions and Reformatsky Reagents with a Sterically Hindered Ketone and Enone", *The Journal of Organic Chemistry* 54: 1992–1997, 1989):

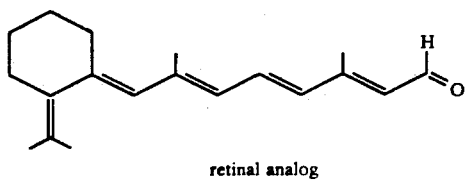

retinal analog

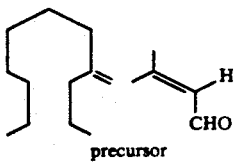

precursor

A precursor to this retinal analog has been reported in this publication.

Since vitamin A is known to play a role in the visual cycle in vertebrates, vitamin A and its analogs have been used to treat vision-related problems. Vitamin A has also been associated with bioactive properties useful in cancer chemoprevention, chemotherapy, treatment of dermatological disorders (e.g., with "Retin-A" TM and "Accutane" TM) and immunostimulation. However, the therapeutic index of vitamin A, which is a function of its potency and toxicity, limits the applications thereof.

SUMMARY OF THE INVENTION

According to the present invention, a first series of retinoids is produced, in which the compounds have the following general structure:

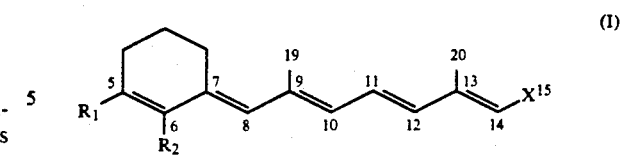

wherein $R_1$ and $R_2$ are independently selected from the group consisting of a hydrogen atom, a $C_{1-4}$ alkyl, a $C_{1-4}$ alkenyl and a $C_{1-4}$ alkoxy, or $R_1$ and $R_2$ taken together are fused to form a 5- to 7-membered cycloakyl or cycloalkenyl ring; and X is $CO_2H$ or $CH_2OH$.

Preferably, $R_1$ is selected from the group consisting of a hydrogen atom, a methyl group ($CH_3$), an ethyl group ($CH_3CH_2$) and a n-propyl group ($CH_3CH_2CH_2$), and $R_2$ is selected from the group consisting of a hydrogen atom, a methyl group, an ethyl group, an isopropyl group (($CH_3)_2CH$) and a tert-butyl group (($CH_3)_3C$), or $R_1$ and $R_2$ taken together form a cyclohexene ring.

A second series of retinoid compounds in accordance with our invention has the following general formula:

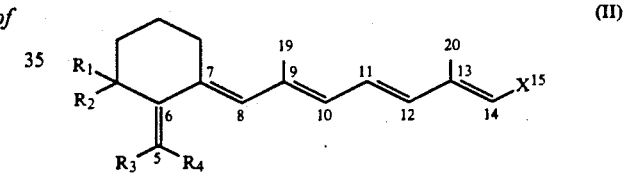

wherein $R_1$, $R_2$, $R_3$ and $R_4$ are independently selected from the group consisting of a hydrogen atom, a $C_{1-4}$ alkyl, a $C_{1-4}$ alkenyl and a $C_{1-4}$ alkoxy, or $R_2$ and $R_3$ taken together are fused to form a 5- to 7-membered cycloalkyl or cycloalkenyl ring and $R_1$ and $R_4$ are as above; and X is $CO_2H$ or $CH_2OH$.

Preferably, $R_1$ is a hydrogen atom or a methyl group, $R_2$ is a hydrogen atom, a methyl group, an ethyl group or an n-propyl group ($CH_3CH_2CH_2$), $R_3$ is a hydrogen atom, a methyl group, or an ethyl group, and $R_4$ is a hydrogen atom or a methyl group; or $R_2$ and $R_3$ taken together form a cyclohexene ring with $R_1$ and $R_4$ being a methyl group.

The compounds (I) and (II) according to this invention are useful as chemopreventive and chemotherapeutic cancer-treating agents. Thus, the retinoids of the invention have utilities as chemopreventive agents for inhibiting the growth of cancerous tumors including skin, bladder and mammary cancers, and as chemotherapeutic agents for treating existing cancers. The retinoids also can be administered as general immunostimulants and as dermatological agents for treating skin disorders including skin aging.

DESCRIPTION OF PREFERRED EMBODIMENTS

Preferably, the series (I) and (II) compounds are selected from among the following species, with compounds 1-12 in series (I) and compounds 13-24 in series (II):

of Series I have a cyclohexane ring structure which exclusively maintains the 6-s-trans geometry between

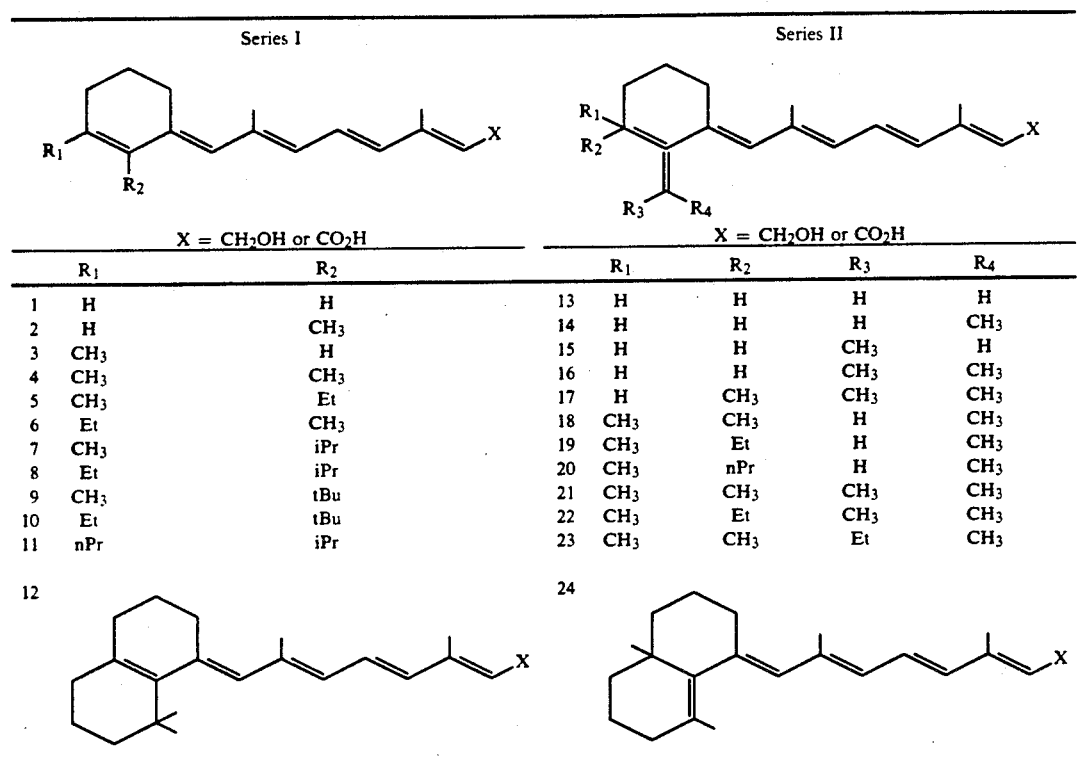

| Series I | | | Series II | | | | |
|---|---|---|---|---|---|---|---|
| X = CH₂OH or CO₂H | | | X = CH₂OH or CO₂H | | | | |
| | R₁ | R₂ | | R₁ | R₂ | R₃ | R₄ |
| 1 | H | H | 13 | H | H | H | H |
| 2 | H | CH₃ | 14 | H | H | H | CH₃ |
| 3 | CH₃ | H | 15 | H | H | CH₃ | H |
| 4 | CH₃ | CH₃ | 16 | H | H | CH₃ | CH₃ |
| 5 | CH₃ | Et | 17 | H | CH₃ | CH₃ | CH₃ |
| 6 | Et | CH₃ | 18 | CH₃ | CH₃ | H | CH₃ |
| 7 | CH₃ | iPr | 19 | CH₃ | Et | H | CH₃ |
| 8 | Et | iPr | 20 | CH₃ | nPr | H | CH₃ |
| 9 | CH₃ | tBu | 21 | CH₃ | CH₃ | CH₃ | CH₃ |
| 10 | Et | tBu | 22 | CH₃ | Et | CH₃ | CH₃ |
| 11 | nPr | iPr | 23 | CH₃ | CH₃ | Et | CH₃ |

In both series, the higher the number of the compound, the more preferred is the species due to better properties. With respect to series (I), compounds 7-12 are the preferred species. In series (II), compounds 17-24 are the preferred species. The inventive retinoids the ring and the polyene chain, whereas the inventive series II retinoid maintain the 6-s-cis geometry.

The inventive retinoids are synthesized in accordance with the following general reaction scheme:

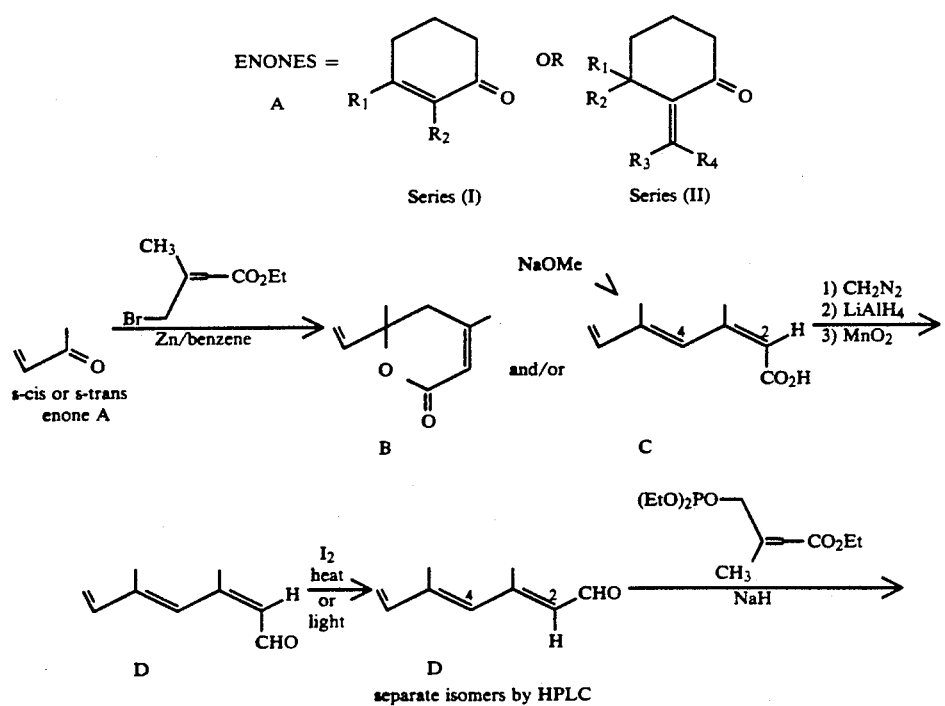

-continued

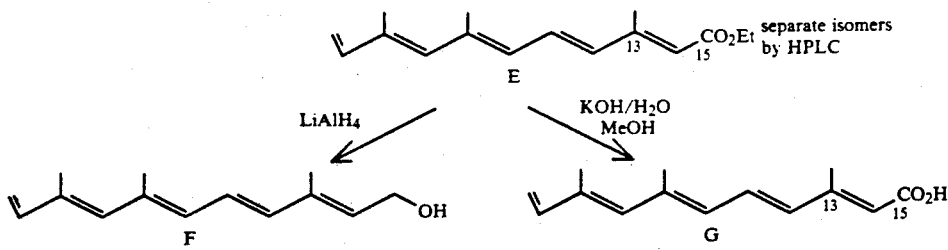

In the following description, all percentages are by weight unless otherwise indicated.

A series I or II enone A is first reacted under Reformatsky conditions. For the series I enone A, $R_1$ and $R_2=H$, $C_{1-4}$ alkyl, $C_{1-4}$ alkenyl or simple alkoxy, or $R_1$ and $R_2$ form a 5- to 7-membered cycloalkyl or cycloalkenyl. For the series II enone A, $R_1$ to $R_4=H$, $C_{1-4}$ alkyl, $C_{1-4}$ alkenyl or simple alkoxy, or $R_2$ and $R_3$ form a 5- to 7-membered cycloalkyl or cycloalkenyl.

Thus, to a mixture of freshly activated zinc in benzene at 85° C. is added in portions a solution of enone A and ethyl bromosenecioate in benzene. After the first portion is added, a crystal of $I_2$ is added to initiate the reaction. This provides a mixture of lactone B and carboxylic acid C. The carboxylic acid C is separated by extraction of an ether solution into 5% NaOH. Lactone B is then completely converted into the carboxylic acid C by treatment with $NaOCH_3$ in $CH_3OH$.

The carboxylic acid C is then reacted with diazomethane to provide the methyl ester, and an ether solution of the methyl ester is reduced with $LiAlH_4$ at $-25°$ C. to provide the alcohol. A methylene chloride solution of the alcohol is oxidized with $MnO_2$ at 0° C. to give aldehyde D as the (2Z) isomer. A solution of the (2Z)-D compound in chloroform containing 0.5% $I_2$ is then placed 3 inches from a 105-watt tungsten lamp and irradiated to provide (2E,4E)-D. Unreacted (2Z)-D is recycled for complete conversion to the (2E,4E) aldehyde D. The (2E,4)-D compound is purified by preparative chromatography on silica gel (10% acetone/hexane). A solution of the (2E,4E)-D compound in THF next undergoes Horner-Emmons condensations (see, e.g.: Isler, Carotenoids, Birkhauser Verlag: Basel 1971; Vaezi et al., Org. Prep. Proc. Int. 19: 187, 1987) with triethylphosphonosenecioate and NaH at 0° C. to yield ester E. The individual geometrical isomers are separated on a silica gel HPLC column using 1.0% $Et_2O$/hexane to give predominantly (all E)-and (13Z)-E. The corresponding isomers of acid G are prepared by hydrolysis of E in refluxing aqueous $KOH/CH_3OH$ for one hour. Finally, the isomers of E are each converted to the corresponding isomers of alcohols F by reduction with $LiAlH_4$. Also, (2Z)-D can be carried on as indicated for (all E)-D (without the $I_2$-catalyzed isomerization) to provide the (9Z)- and (9Z,13Z)-isomers of F and G.

EXAMPLE

A synthetic procedure for producing the retinoid 7 of series (I), wherein $X=CO_2H$, is illustrated below:

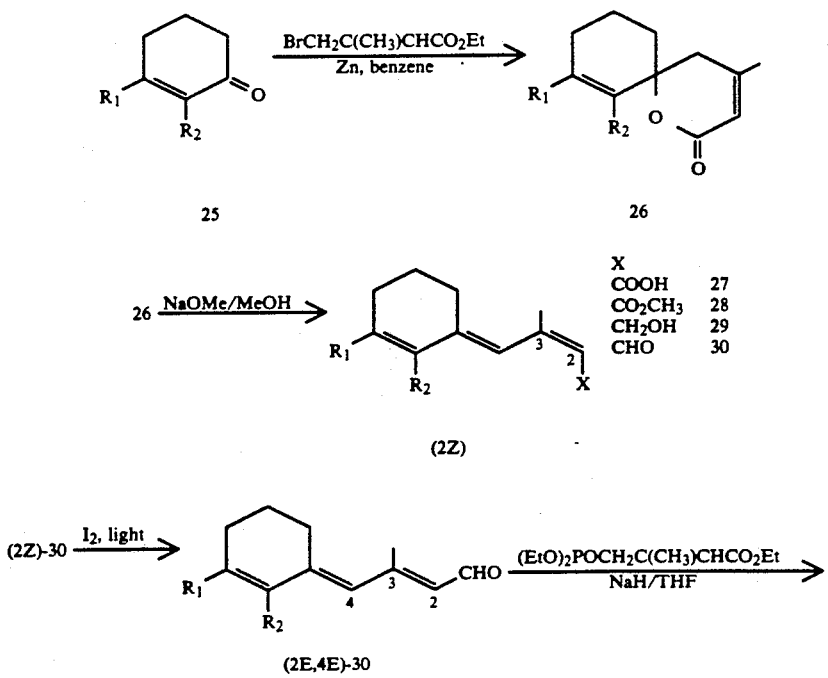

-continued

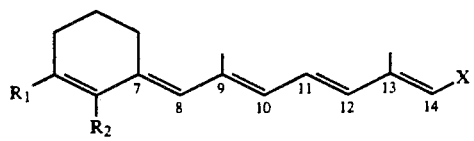

| X | |
|---|---|
| CO$_2$Et | 31 |
| CO$_2$H | 7 |
| CH$_2$OH | 7 |

(all E) and (13Z) isomers

Ketone 25 (formula (I): R$_1$=CH$_3$ and R$_2$=iPr) was first reacted under Reformatsky conditions. Thus, to a mixture of freshly activated zinc in benzene at 85° C. was added in portions a solution of ketone 25 and ethyl bromosenecioate in benzene. After the first portion was added, a crystal of I$_2$ was added. This provided a mixture of lactone 26 and carboxylic acid 27. The latter was separated by extraction of an ether solution into 5% NaOH. The lactone 26 was then completely converted into the acid 27 by treatment with NaOCH$_3$ in CH$_3$OH. The yield of the acid 27 from the ketone 25 was 66%.

The carboxylic acid 27 was then reacted with diazomethane to provide methyl ester 28 in 94% yield. An ether solution of the ester 27 was reduced with LiAlH$_4$ at −25° C. to produce alcohol 29 (94% yield). A methylene chloride solution of alcohol 29 was oxidized with MnO$_2$ at 0° C. to give aldehyde 30 with a yield of 76%. The aldehyde 30 was shown by NMR studies to exist exclusively as the (2Z) isomer.

A solution of the aldehyde 30 in chloroform containing 0.5% I$_2$ was then placed three inches from a 105-watt tungsten lamp and irradiated to provide the (2E,-4E)-30. Unreacted aldehyde (2Z)-30 was recycled so that the conversion to isomer (2E,4E)-30 was 100%. The isomer (2E,4E)-30 was purified by preparative chromatography on silica gel (10% acetone/hexane). A solution of compound (2E,4E)-30 in THF then underwent Horner-Emmons condensation with triethylphosphonosenecioate and NaH at 0° C. to give ester 31 (80–95% yield).

The individual geometrical isomers of ester 31 were separated on a silica gel HPLC column using 1.0% Et$_2$OH/hexane to give (all E)- and (13Z)-31. (All E)- and (13Z)- acids 7 (92–99% yield), wherein the polar group X is a carboxylic group, were prepared by hydrolysis of the individual isomers of 31 in refluxing aqueous KOH/CH$_3$OH for one hour. Esters 31 were respectively converted to (all E)- and (13Z)-alcohols 7 (96–98% yield), wherein X is an alcohol group CH$_2$OH, by reduction with LiAlH$_4$ as above. (2Z)-30 was also carried on as above without I$_2$-catalyzed isomerization to give (9Z)- and (9Z,13Z)-7.

The compounds (all E)-7 and (13Z)-7 shown in the reaction scheme are the isomers of retinoid 7 of series (I). Structural representations of the isomers of retinoid 7 are shown below:

Retinoids control = (all E)-retinoic acid (all E)-7 with X = CO$_2$H

-continued
Retinoids (9Z)-7 with X = CO$_2$H (13Z)-7 with X = CO$_2$H (9Z,13Z)-7 with X = CO$_2$H The synthesized retinoids were tested for their bioactive properties. Experimental results are summarized in Table 1 and FIG. 1.

ODC Assay Study:

An in vivo ODC assay was conducted using four configurational isomers of retinoid 7 with X=CO$_2$H to study their bioactivities with respect to prevention of tumors. The ODC assay measured the inhibition by retinoids of the induction of ornithine decarboxylase in mouse epidermis by phorbol ester (TPA), an indicator of retinoid potency as a chemopreventive agent.

Inhibition of 12-O-tetradecanoyl-phorbol-13-acetate (TPA)-induced ornithine decarboxylase (ODC) activity of the retinoids was studied according to the procedure of Verma and Boutwell ("Vitamin A acid (retinoic acid), a potent inhibitor of 12-O-tetradecanoyl-phorbol-13-acetate-induced ornithine decarboxylase activity in mouse epidermis", *Cancer Research* 37: 2196–2201, 1977), with the following modifications. A single application of TPA was made to the shaved backs of CD-1 mice 30 to 60 minutes after a single application of the test retinoid. Five hours after the application of TPA, the exposed skins from the back of the three animals in each group were collected, and the epidermal extracts prepared from each animal were pooled and assayed. In order to improve the counting efficiency of radiolabeled product formed in the assay, the specific activity of $^{14}$C-ornithine was increased five-fold; the assay was terminated by the addition of citric acid at 45 minutes to ensure linear kinetics.

CRABP Assay Study:

A standard in vitro cellular retinoic acid binding protein (CRABP) assay was also conducted on the retinoids. The CRABP binding study measured the ability of retinoids to compete for the retinoic acid binding site on CRABP, also a good indicator of retinoid potency as a chemopreventive agent.

Binding affinities of the retinoids for CRABP from chick embryo skin were determined by the sucrose density gradient technique (Sani et al., "Determination of binding affinities of retinoids to retinoic acid-binding protein and serum albumin", Biochem. J. 171: 711–717, 1978). Aliquots (2 mg protein) of chick skin extracts were incubated with 300 pmoles of [$^3$H] retinoic acid in the presence or absence of 100-fold molar excesses of the test compounds. The 2S CRABP peaks were determined from the radioactivity profiles obtained after sedimentation through 5 to 20% sucrose density gradients at 180,000×g for 18 hours (Sani et al., supra). In order to calculate the concentrations of retinoids to produce 50% inhibition ($I_{50}$) of binding of [$^3$H] retinoic acid to CRABP, portions of chick embryo skin extract (1 mg protein) were incubated with 100 pmoles of [$^3$H] retinoic acid in the presence or absence of 1-, 5-, 10- and 25-fold molar excesses of unlabeled test retinoids (Sani et al., "Interference of retinoic acid-binding to its binding protein by omega-6 fatty acids", Biochem Biophys Res Comm 147: 25–30, 1987). Free radioactive retinoid was removed by absorption on dextran-coated charcoal. The $I_{50}$ values of the test compounds were derived from the semilog plots of their molar concentrations versus the specifically bound [$^3$H] retinoic acid to CRABP at the different concentrations of the test retinoids.

Table 1 summarizes the ODC inhibitory activity (values normalized to TPA control of 10) and CRABP binding activity for the retinoid compounds 7 with $X=CO_2H$ of the invention:

TABLE 1

| Retinoid | ODC Assay (nmol CO$_2$/30 min./ mg protein) | CRABP $I_{50}$ (μM) |
|---|---|---|
| all-E retinoic acid | 0.5 | 0.9 |
| (all E)-7 | 0.5 | 0.4 |
| (13Z)-7 | 1.0 | 0.5 |
| (9Z)-7 | >100 | 2.8 |
| (9Z,13Z)-7 | >100 | 4.9 |

The bioactivity data in Table 1 indicate that the binding affinity of the all-E isomer of retinoid 7 with $X=CO_2H$ to CRABP is as good as that for the all-E retinoic acid control. (All E)-7 has a slightly higher activity than (all-E)-retinoic acid in the ODC assay. The (13Z)-7 isomer shows slightly less activity than the all-E configuration. The other isomers of retinoid 7, i.e. the (9Z)- and (9Z,13Z)-isomers, were significantly less potent in these tests.

FIG. 1 graphically shows the sucrose density gradient sedimentation patterns illustrating the effect of competition of retinoids on the binding of 300 pmol of [$^3$H] retinoic acid to chick embryo skin CRABP. In FIG. 1, the results for the control without retinoid added (. . .) are shown. All of the other radioactivity profiles are the control plus 100-fold excesses of the following test compounds: x=retinoic acid, ○=(all E)-7, □=(9Z)-7, ●=(13Z)-7 and ■=(9Z,13Z)-7.

The relative binding affinities of the retinoids for CRABP, shown in FIG. 1, demonstrate that whereas retinoid (all E)-7 showed the same degree of inhibition of [$^3$H] retinoic acid-binding to CRABP as retinoic acid itself (i.e., 100%), retinoid (13Z)-7 expressed only 70% binding affinity as compared to that of retinoic acid. Retinoids (9Z)-7 and (9Z,13Z)-7 were virtually without any competition for [$^3$H] retinoic acid-binding sites on CRABP (i.e., 0% inhibition).

Mouse Papilloma Assay Study:

Retinoid (all E)-7 with $X=CO_2H$ was also tested in a mouse papilloma assay. The study was conducted in accordance with Verma et al., "Correlation of the Inhibition by Retinoids of Tumor Promoter-induced Mouse Epidermal Ornithine Decarboxylase Activity and of Skin Tumor Promotion", Cancer Research 39: 419–425, 1979. This assay measured the inhibition of tumor formation following initiation with dimethylbenz(a)anthracene (DMBA).

Retinoic acid reduced tumor production to 11% of controls. In comparison, the (all E)-7 of the invention reduced tumor production to 20% of controls.

In using the novel series (I) and series (II) retinoids as a pharmaceutical or medicament, a therapeutically effective amount of the retinoid is administered to a patient in a manner analogous to that for conventional vitamin A applications. As a skin treatment, the retinoids are expected to be administered topically, e.g. in up to 1% concentrations in an appropriate vehicle. For this and other applications, typical oral doses are expected to range from 0.1 to 100 mg/day of the retinoids.

We claim:

1. A compound according to general structure (I):

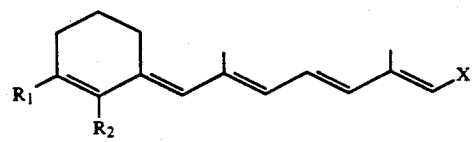

(I)

wherein $R_1$ and $R_2$ are independently selected from the group consisting of a hydrogen atom, a $C_{1-4}$ alkyl group, a $C_{1-4}$ alkenyl group and a $C_{1-4}$ alkoxy group; or $R_1$ and $R_2$ taken together form a 5- to 7-membered cycloalkyl or a 6-membered cycloalkenyl ring; and X is a member selected from the group consisting of a $CO_2H$ group and a $CH_2OH$ group.

2. A compound as recited in claim 1, wherein $R_1$ is selected from the group consisting of a hydrogen atom, a methyl group, an ethyl group and a n-propyl group, and $R_2$ is selected from the group consisting of a hydrogen atom, a methyl group, an ethyl group, an isopropyl group and a tert-butyl group; or $R_1$ and $R_2$ taken together form a cyclohexene ring.

3. A compound as recited in claim 2, wherein $R_1$ is a hydrogen atom and $R_2$ is a hydrogen atom, $R_1$ is a hydrogen atom and $R_2$ is a methyl group, $R_1$ is a methyl group and $R_2$ is a hydrogen atom, $R_1$ is a methyl group and $R_2$ is a methyl group, $R_1$ is a methyl group and $R_2$ is an ethyl group, $R_1$ is an ethyl group and $R_2$ is a methyl group, $R_1$ is a methyl group and $R_2$ is an group, $R_1$ is a methyl group and $R_2$ is a tert-butyl group, $R_1$ is an ethyl group and $R_2$ is a tert-butyl group, $R_1$ is a n-propyl group and $R_2$ is an isopropyl group, or $R_1$ and $R_2$ taken together form a cyclohexene ring.

4. A compound as recited in claim 3, wherein X is a $CO_2H$ group.

5. A compound as recited in claim 3, wherein X is a $CH_2OH$ group.

6. A compound as recited in claim 3, wherein $R_1$ is a methyl group and $R_2$ is an isopropyl group, $R_1$ is an ethyl group and $R_2$ is an isopropyl group, $R_1$ is a methyl group and $R_2$ is a tert-butyl group, $R_1$ is an ethyl group and $R_2$ is a tert-butyl group, $R_1$ is a n-propyl group and $R_2$ is an isopropyl group, or $R_1$ and $R_2$ taken together form a cyclohexene ring.

7. A compound as recited in claim 6, wherein X is a $CO_2H$ group.

8. A compound as recited in claim 6, wherein X is a $CH_2OH$ group.

9. A compound as recited in claim 1, which is the 13Z isomer of said general structure (I).

10. A compound as recited in claim 9, wherein $R_1$ is a methyl group and $R_2$ is an isopropyl group.

11. A compound as recited in claim 10, wherein X is a $CO_2H$ group.

12. A compound as recited in claim 1, which is the all-E isomer of said general structure (I).

13. A compound as recited in claim 12, wherein $R_1$ is a methyl group and $R_2$ is an isopropyl group.

14. A compound as recited in claim 13, wherein X is a $CO_2H$ group.

15. A compound according to formula (II):

(II)

wherein $R_1$, $R_2$, $R_3$ and $R_4$ are independently selected from the group consisting of a hydrogen atom, a $C_{1-4}$ alkyl group, a $C_{1-4}$ alkenyl group and a $C_{1-4}$ alkoxy group; or $R_2$ and $R_3$ taken together form a 5- to 7-membered cycloalkyl or cycloalkenyl a 6-membered ring and $R_1$ and $R_4$ are independently selected from the group consisting of a hydrogen atom, a $C_{1-4}$ alkyl group, a $C_{1-4}$ alkenyl group and a $C_{1-4}$ alkoxy group; and X is a member selected from the group consisting of a $CO_2H$ group and a $CH_2OH$ group.

16. A compound as recited in claim 15, wherein $R_1$ is a member selected from the group consisting of a hydrogen atom and a methyl group, $R_2$ is a member selected from the group consisting of a hydrogen atom, a methyl group, an ethyl group and an n-propyl group, $R_3$ is a member selected from the group consisting of a hydrogen atom, a methyl group, and an ethyl group, and $R_4$ is a member selected from the group consisting of a hydrogen atom and a methyl group; or $R_2$ and $R_3$ taken together form a cyclohexene ring and $R_1$ and $R_4$ are each a methyl group.

17. A compound as recited in claim 16, wherein $R_1$ is a hydrogen atom, $R_2$ is a hydrogen atom, $R_3$ is a hydrogen atom and $R_4$ is a hydrogen atom; $R_1$ is a hydrogen atom, $R_2$ is a hydrogen atom, $R_3$ is a hydrogen atom and $R_4$ is a methyl group; $R_1$ is a hydrogen atom, $R_2$ is a hydrogen atom, $R_3$ is a methyl group and $R_4$ is a hydrogen atom; $R_1$ is a hydrogen atom, $R_2$ is a hydrogen atom, $R_3$ is a methyl group and $R_4$ is a methyl group; $R_1$ is a hydrogen atom, $R_2$ is a methyl group, $R_3$ is a methyl group and $R_4$ is a methyl group; $R_1$ is a methyl group, $R_2$ is a methyl group, $R_3$ is a hydrogen atom and $R_4$ is a methyl group; $R_1$ is a methyl group, $R_2$ is an ethyl group, $R_3$ is a hydrogen atom and $R_4$ is a methyl group; $R_1$ is a methyl group, $R_2$ is a n-propyl group, $R_3$ is a hydrogen atom and $R_4$ is a methyl group; $R_1$ is a methyl group, $R_2$ is a methyl group, $R_3$ is a methyl group and $R_4$ is a methyl group; $R_1$ is a methyl group, $R_2$ is an ethyl group, $R_3$ is a methyl group and $R_4$ is an ethyl group; $R_1$ is a methyl group, $R_2$ is a methyl group, $R_3$ is an ethyl group and $R_4$ is a methyl group; or $R_2$ and $R_3$ taken together form a cyclohexene ring and $R_1$ and $R_4$ are each a methyl group.

* * * * *